United States Patent
Kepes et al.

[11] Patent Number: 5,858,014
[45] Date of Patent: Jan. 12, 1999

[54] ABSORBENT PADS FOR THE BREAST

[76] Inventors: Vince Kepes; Marianna Kepes, both of 4617 Waterford Cir., Stow, Ohio 44224

[21] Appl. No.: 822,994

[22] Filed: Mar. 21, 1997

[51] Int. Cl.⁶ .................................................. A61F 13/15
[52] U.S. Cl. ..................... 604/387; 601/385.1; 601/386
[58] Field of Search .................................. 128/888, 889, 128/890, 893, 894; 604/346, 385.1, 386, 389, 355–357, 387; 450/36–37, 54–57, 81, 53, 92–93

[56] References Cited

U.S. PATENT DOCUMENTS

| | | | |
|---|---|---|---|
| 2,079,426 | 5/1937 | Schottenfels | 450/81 |
| 2,432,559 | 12/1947 | Clarke | 128/894 |
| 2,869,553 | 1/1959 | D'Or | 450/81 |
| 2,915,067 | 12/1959 | Bracht | 450/53 |
| 3,054,400 | 9/1962 | Lizio | 450/81 |
| 4,298,008 | 11/1981 | Kylberg | 450/53 |
| 4,553,550 | 11/1985 | Hattori | 450/81 |
| 4,674,510 | 6/1987 | Sneider | 450/57 |
| 5,326,308 | 7/1994 | Fochler | 450/37 |
| 5,441,436 | 8/1995 | Moretz et al. | 450/37 |
| 5,603,653 | 2/1997 | Hartman | 450/56 |
| 5,664,984 | 9/1997 | Laughridge | 450/56 |

Primary Examiner—John G. Weiss
Assistant Examiner—K. M. Reichle
Attorney, Agent, or Firm—Renner, Kenner, Greive, Bobak, Taylor & Weber

[57] ABSTRACT

A breast pad for absorbing moisture around a breast area supported by a brassiere, is provided by a layer of absorbent material, a layer of moisture retention material and a base layer having at least partially disposed on one side thereof a releasable adhesive material, wherein the releasable adhesive material is affixed to a cup surface of a brassiere so that said absorbent material is in contact with skin around the breast area. The material may be provided with notches to allow conformance of the material to the shape of the brassiere and with attachment tabs to assist in positioning the layer of absorbent material. Another embodiment of the breast pad for absorbing moisture around a breast area may provide layers of substantially absorbent material disposed on opposite sides of a moisture retention layer having two opposed longitudinal edges joined at opposed ends, the layers of absorbent material positioned adjacent the breast and the midriff to absorb moisture. The longitudinal edges may be provided with notches to conform the material to the underside of the breast or the longitudinal edges may be provided in a concavo-convex configuration. Adjacent breast pads may be joined by an attachment flag extending from one end thereof.

6 Claims, 4 Drawing Sheets

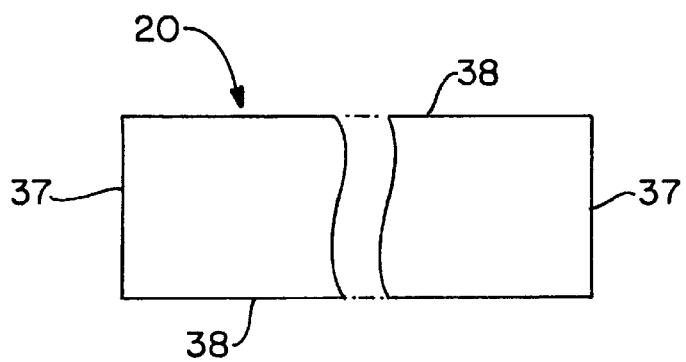
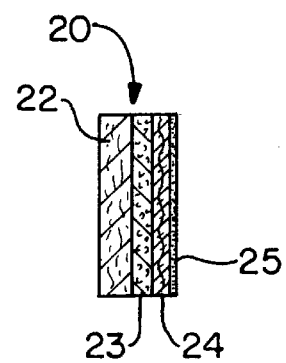
FIG.-1
FIG.-2
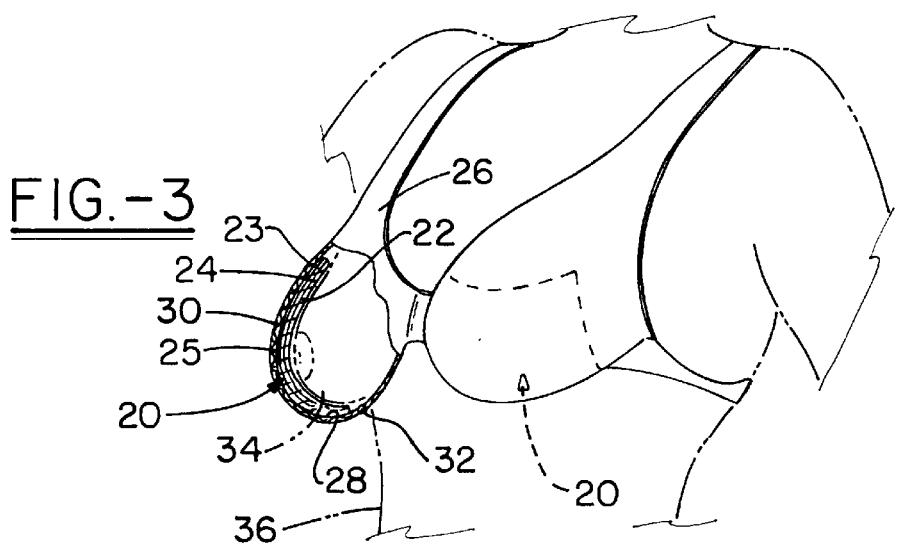
FIG.-3
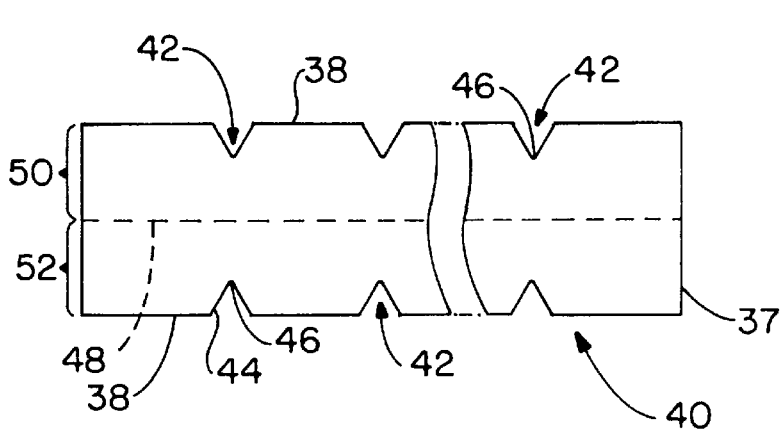
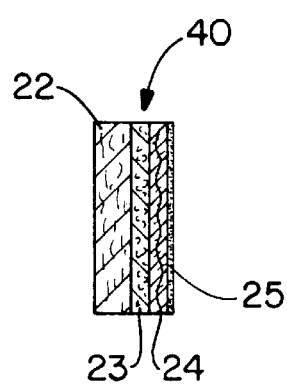
FIG.-4
FIG.-5

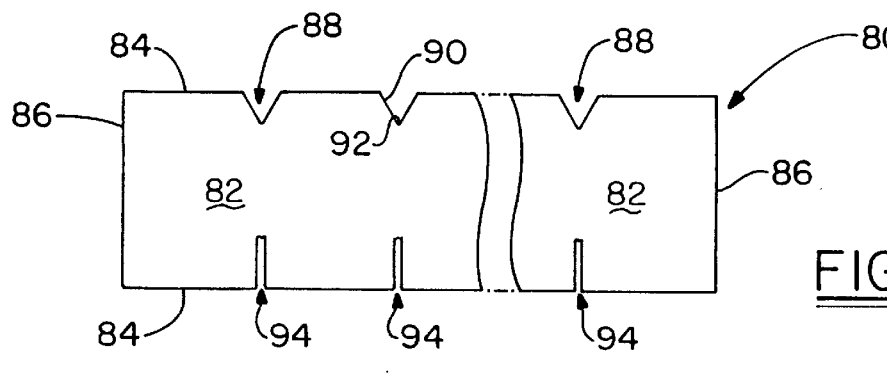
FIG.-12
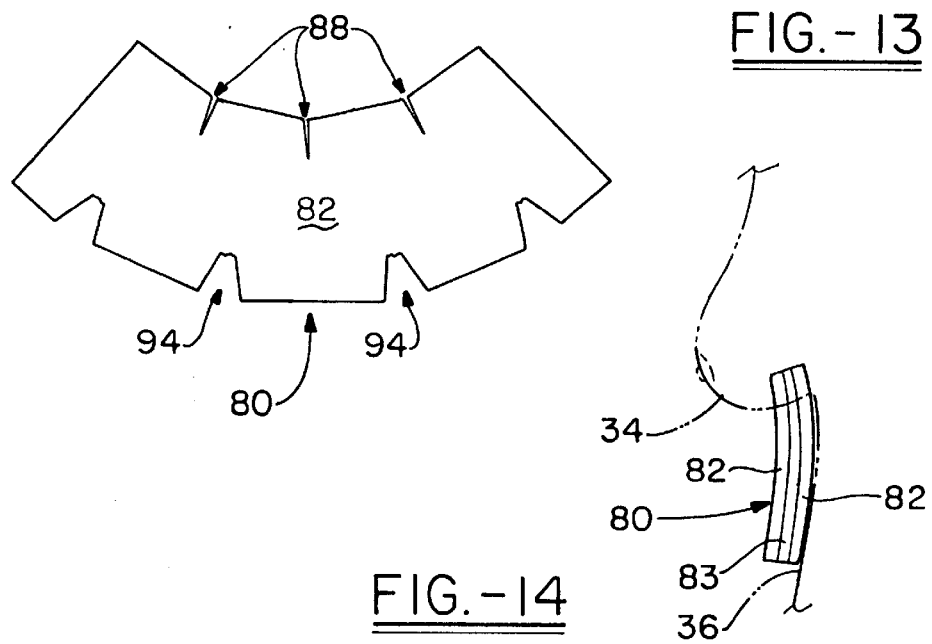
FIG.-13
FIG.-14
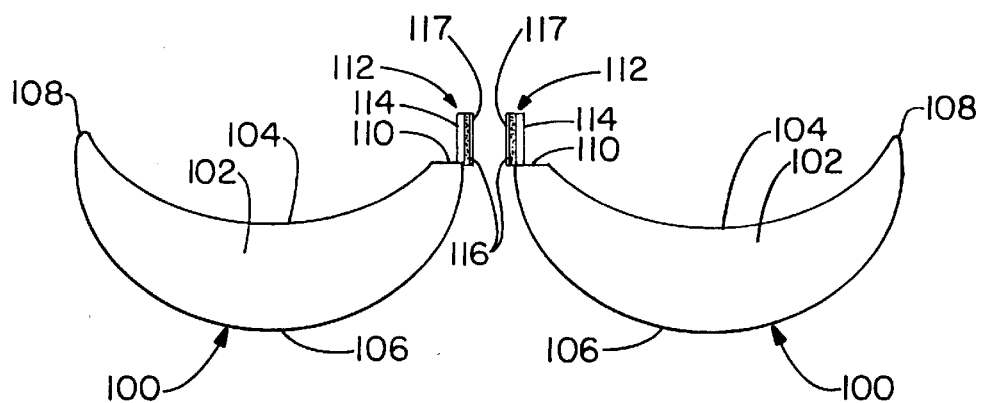
FIG.-15

ABSORBENT PADS FOR THE BREAST

TECHNICAL FIELD

The present invention herein resides in the art of undergarments. More particularly, the present invention relates to padding that may be positioned and flexed to fit under the breast and/or inside a brassiere to absorb sweat or breast milk to prevent rashes and infection of skin on and near the breast.

BACKGROUND ART

When exercising or nursing it is common for excess moisture, either sweat or breast milk, to gather on or between the breast and the midriff. If this excess moisture is not wiped away or absorbed immediately it may cause inflammation of the exposed skin. Evaporation of the excess moisture may remove oils from the skin and cause it to dry and chafe. These problems can be further exacerbated by wires contained within the brassiere or rough fabric edges of the brassiere. In the case of a nursing mother, this dryness or inflammation can lead to an infection of the breast, which in turn causes the mother great discomfort and sickness while nursing her child. As a result, the mother may no longer want to nurse the child, thus the child would lose the important health benefits derived from nursing. Nor can the mother take any medication to relieve her suffering as the medicine may adversely affect her child. In the case of a heavy-set person, excess moisture may cause discomfort or irritability after the unabsorbed moisture dries on the skin.

Nursing brassieres are available to absorb some excess moisture; however, for some mothers they are inadequate. It is also known to employ small towels or other cloth-like material between the breast and the brassiere. Unfortunately, not all of the skin is in contact with the material to absorb the excess moisture or the towel may pull away during nursing or exercising leaving the previously protected area exposed. Moreover, even if the towel absorbs the excess moisture, the wet towel may remain in contact with the skin and cause irritation. It will also be appreciated that towels or drying powders used may cause the skin to become too dry, which also in turn leads to inflammation of the skin.

Clearly there is a need in the art for an absorbent breast pad that eliminates skin rashes and inflammation. Moreover, there is a need in the art for an absorbent breast pad that conforms to the shape of the underside of the breast and that may be attached to a cup of a brassiere. There is also a need for an absorbent breast pad that draws excess moisture away from the skin and prevents the moisture from further contacting the skin.

DISCLOSURE OF INVENTION

In light of the foregoing it is a first aspect of the present invention to provide an absorbent breast pad.

Another aspect of the present invention is to provide a breast pad that has an absorbent layer, a moisture retention layer and a base layer with a releasable adhesive, wherein the releasable adhesive is temporarily attachable to a cup of a brassiere and wherein the absorbent layer is placed adjacent the breast and midriff to draw excess moisture away from the skin and transfers the excess moisture to the moisture retention layer.

Still another aspect of the present invention, as set forth above, is to provide a plurality of notches along at least one longitudinal edge of the breast pad to allow curvature and conformance to the shape of the underside of the breast.

Yet another aspect of the present invention, as set forth above, is to provide a plurality of slits along an opposite longitudinal edge of the breast pad to assist in the conformance of the breast pad, wherein the breast pad may be positioned between the breast and the brassiere or between the breast and the midriff.

A further aspect of the present invention, as set forth above, is to provide a plurality of attachment tabs extending from one of the longitudinal edges, wherein one side of the attachment tabs has a releasable adhesive thereon that is attachable to a cup of the brassiere.

Still a further aspect of the present invention, as set forth above, is to provide substantially crescent-shaped breast pads which have a moisture retention layer disposed between absorbent layers, wherein the breast pads are disposed between the breast and the midriff.

Yet a further aspect of the present invention, as set forth above, is to provide extending tabs with releasable adhesive for attaching adjacent crescent-shaped breast pads to one another.

The foregoing and other aspects of the present invention which shall become apparent as the detailed description proceeds are achieved by a breast pad for absorbing moisture around a breast area supportable by a brassiere, comprising a layer of absorbent material adjacent a layer of moisture retention material having at least partially disposed on one side thereof a releasable adhesive material, wherein the releasable adhesive material is affixable to a cup surface of a brassiere so that said layer of absorbent material is in contact with skin around the breast area when worn.

Other aspects of the present invention are attained by a breast pad for absorbing moisture between a breast and a midriff, comprising at least one layer of absorbent material adjacent a layer of moisture retention material having two opposed longitudinal edges joined at opposed ends, said layers positioned between the breast and the midriff to absorb moisture.

BRIEF DESCRIPTION OF THE DRAWINGS

For a complete understanding of the objects, techniques and structure of the invention reference should be made to the following detailed description and accompanying drawings wherein:

FIG. 1 is an elevational view of an absorbent breast pad according to the present invention usable in conjunction with a brassiere;

FIG. 2 is an enlarged sectional view of the absorbent breast pad;

FIG. 3 is a schematic side view in cross-section of the breast pad in use;

FIG. 4 is an elevational view of an absorbent breast pad according to a first alternative embodiment of the present invention;

FIG. 5 is an enlarged sectional view of the first alternative embodiment;

FIG. 12 is an elevational view of an absorbent breast pad used without a brassiere according to the present invention;

FIG. 13 is a schematic front view of the embodiment shown in FIG. 12;

FIG. 14 is a schematic side view in cross-section of the embodiment shown in FIG. 13 in use;

FIG. 15 is an elevational view of another absorbent breast pad used without a brassiere according to the present invention;

BEST MODE FOR CARRYING OUT THE INVENTION

Figure 6:
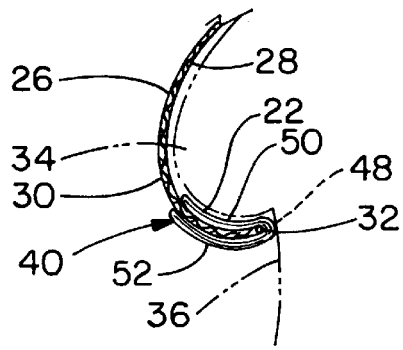
FIG. 6 is a side sectional view of the first alternative embodiment in position for use.

Referring now to the drawings and more particularly to FIGS. 1–3, it can be seen that an absorbent breast pad according to the present invention is designated generally by the numeral 20. As shown, the pad 20 includes a layer of absorbent material 22 attached and adjacent to a layer of moisture retention material 23 which is attached and adjacent to a base layer 24. A releasable adhesive 25 is selectively disposed on all or a portion of a side of the base layer 24 facing away from the layer of moisture retention material 23. The breast pad 20 is employed for use in conjunction with a brassiere 26 which has an inner cup surface 28 opposite an outer cup surface 30. A wire or seam 32 joins the inner cup surface 28 to the outer cup surface 30 in a manner well known in the art. As is well known, the brassiere 26 lifts a breast 34 away from a midriff 36. The breast pad 20, which includes opposed ends 37 connected by opposed longitudinal edges 38, is inserted between the breast 34 and the brassiere 26 as schematically shown in FIG. 3. It will be appreciated that the ends 37 and the edges 38 may be sealed to secure the layers 23-25 to one another to prevent their separation or fraying. The releasable adhesive 25 is positioned upon the inner cup surface 28 so that one of the longitudinal edges 38 is proximally parallel with the length of the wire or seam 32. Accordingly, the layer of absorbent material 22 is placed adjacent the underside of the breast 34 to absorb any excess moisture, which is then drawn into and held by the layer of moisture retention material 23. In essence, the layer 22 functions as a conduit to move the excess moisture from the skin to the layer of moisture retention material 23. The breast pads disclosed herein function by capillary action to provide comfort to the user. In other words, the layer of absorbent material 22 wicks excess moisture into the layer of moisture retention material 23 and holds the excess moisture away from the skin.

It will be appreciated that the breast pad 20 is typically provided in disposable form such that an unused breast pad 20 is placed upon the inner cup surface 28 prior to wearing of the brassiere 26. With the breast pad 20 properly positioned, any excess moisture that develops from exercising or from a mother nursing her baby is absorbed and held so that the moisture does not accumulate and dry upon the skin of the breast. It will be appreciated that only excess moisture is drawn away from the skin by the layer 23 so as not to dry out and irritate the skin adjacent the absorption layer 22. After a predetermined period of time or whenever the layer of retention material 23 is no longer effective, the breast pad 20 is removed from the brassiere 26 and a new breast pad 20 may be inserted. It will be appreciated that the length of the breast pad 20 may be varied for the desired amount of coverage. Additionally, the longitudinal edges 38 may be positioned anywhere within the brassiere 26 found to be most comfortable.

One variation of the breast pad, with many of the same attributes as above, is presented in FIGS. 4–7 and is generally designated by the numeral 40. The breast pad 40, as in the previous embodiment, includes a layer of absorbent material 22, a layer of moisture retention material 23 and a base layer 24 with a releasable adhesive material 25 thereon. Disposed along both longitudinal edges 38 are a plurality of notches 42 which are generally v-shaped. Of course, shapes other than a "v" may be employed for the notches 42. Each notch 42 includes a pair of notch edges 44 that terminate at a vertex 46. Each vertex 46 is aligned with a vertex 46 from an opposed notch 42 from the opposed longitudinal edge 38. A fold line 48 is provided at about a midpoint substantially parallel with and between the longitudinal edges 38. As such, the base layer 24 with releasable adhesive material 25 is divided at the fold line 48 into a first portion 50 and a second portion 52.

Figure 7:
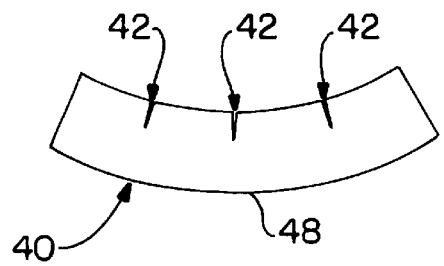
FIG. 7 is a front view of the first alternative embodiment in use.
Figure 8:
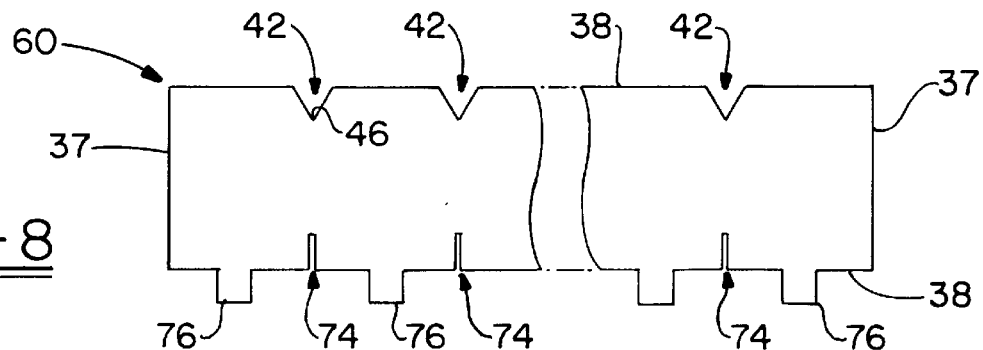
FIG. 8 is an elevational view of an absorbent breast pad according to a second alternative embodiment of the present invention.
Figure 9:
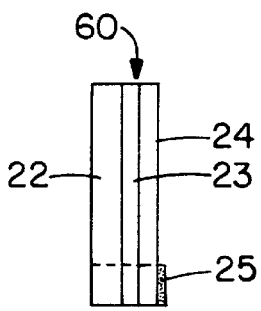
FIG. 9 is an enlarged side view of the second alternative embodiment.

As best seen in FIGS. 6 and 7, the breast pad 40 is affixed to a brassiere 26 by applying the first portion 50 to the inner cup surface 28 and the second portion 52 to the outer cup surface 30. As such, the fold line 48 is placed substantially along the length of the wire or seam 32. Accordingly, the layer of absorbent material 22 is placed adjacent to the underside of the breast 34 and the midriff 36 so that the area underneath the brassiere may also be provided with a means for absorbing and retaining excess moisture. It will be appreciated that the notches 42, when the pad 40 is folded at the fold line 48, may be curved upwardly so that the notch edges 44 are positioned closer to one another as best seen in FIG. 7. The v-shape notches 42 allow the breast pad 40 to be selectively curved by controlling the spacing between the notch edges 44. This allows the breast pad 42 to conform to the shape of the wire or seam 32 and provide a more comfortable fit. This also ensures a maximum amount of moisture absorption and retention as excess moisture tends to accumulate along the seam area.

Figure 10:
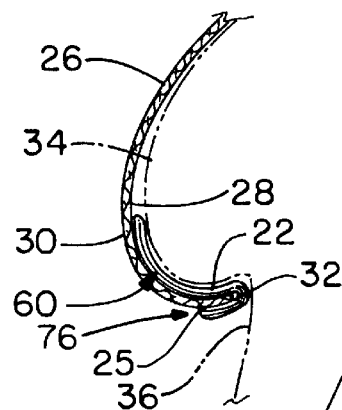
FIG. 10 is a sectional side view of the second alternative embodiment in positional for use.
Figure 11:
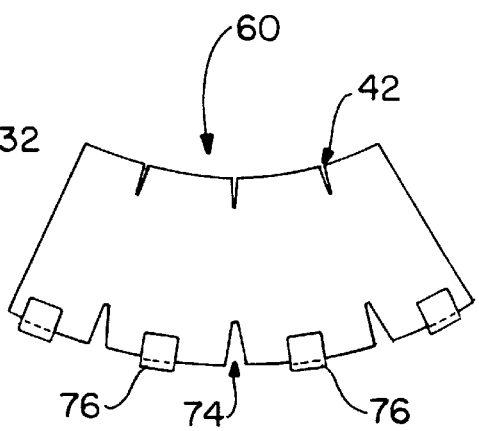
FIG. 11 is a schematic front view of the second alternative embodiment in use.

Referring now to FIGS. 8–11, it can be seen that a second alternative embodiment of a breast pad, with many of the same attributes as the other embodiments, is designated generally by the numeral 60. The breast pad 60 includes a layer of absorbent material 22, a layer of moisture retention material 23 and a base layer 24. The breast pad 60 has opposed longitudinal edges 38 connected by opposed ends 37. A plurality of notches 42 are provided along one of the longitudinal edges 38 and are substantially v-shaped. Each notch 42 provides a pair of notch edges 44 which are connected at a vertex 46. Disposed along the opposite longitudinal edge 38 is a slit 74 which is substantially opposite the vertex 46 of the corresponding notch 44 on the other longitudinal edge. Disposed between each slit 74 along the opposite longitudinal edge 38 and extending downwardly therefrom is an attachment tab 76 that includes a layer of releasable adhesive material 25 selectively disposed on the base layer 24. As seen in FIGS. 10 and 11, the breast pad 60 is substantially positioned upon the inner cup surface 28 wherein the opposite longitudinal edge 38 is positioned substantially along the wire or seam 32. The attachment tabs 76 are moved or bended such that the releasable adhesive material 25 attaches to the outer cup surface 30. The notches 42 and the slit 74 allow the breast pad 60 to be curved such that the notch edges 44 are directed toward one another and wherein the slits 74 allow the longitudinal edge associated therewith to be deformed such that the edges of the slits separate.

Based upon the structure provided by the breast pads 20, 40 and 60, it will be appreciated that they effectively absorb and retain excess moisture, such as sweat or breast milk, that may otherwise accumulate and irritate the skin around the breast. Accordingly, the risk of inflammation or infection is substantially reduced thereby eliminating undesired discomfort. Another advantage of the breast pads is that they may be provided as a disposable article and used only when needed and may be easily replaced when the effectiveness of the absorbent material has expired. Still another advantage of the present invention is that it can be used relatively inconspicuously and not detract from the appearance of the brassiere 26.

Another embodiment of the breast pad is presented in FIGS. 12–18. These embodiments are provided for use without a brassiere and primarily rely on the weight of the breast against the midriff to hold the pad in place.

Figure 16:
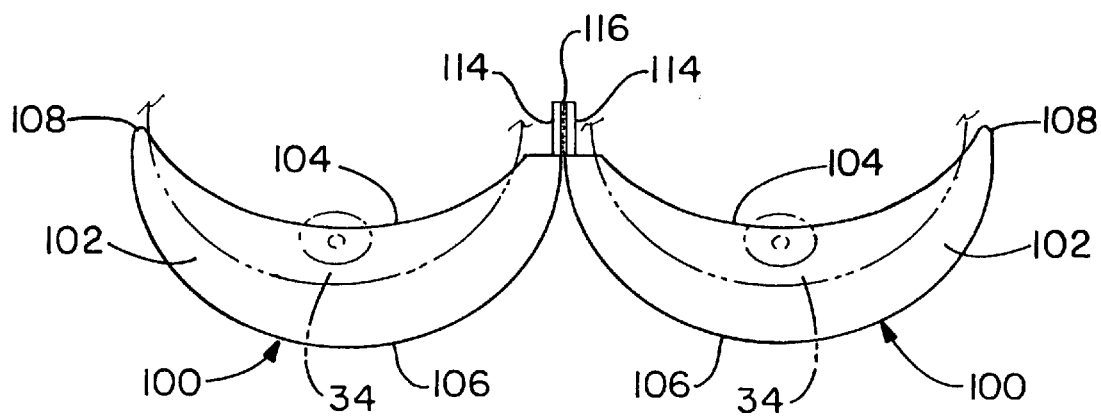
FIG. 16 is a schematic front view of the embodiment shown in FIG. 15 in use.
Figure 17:
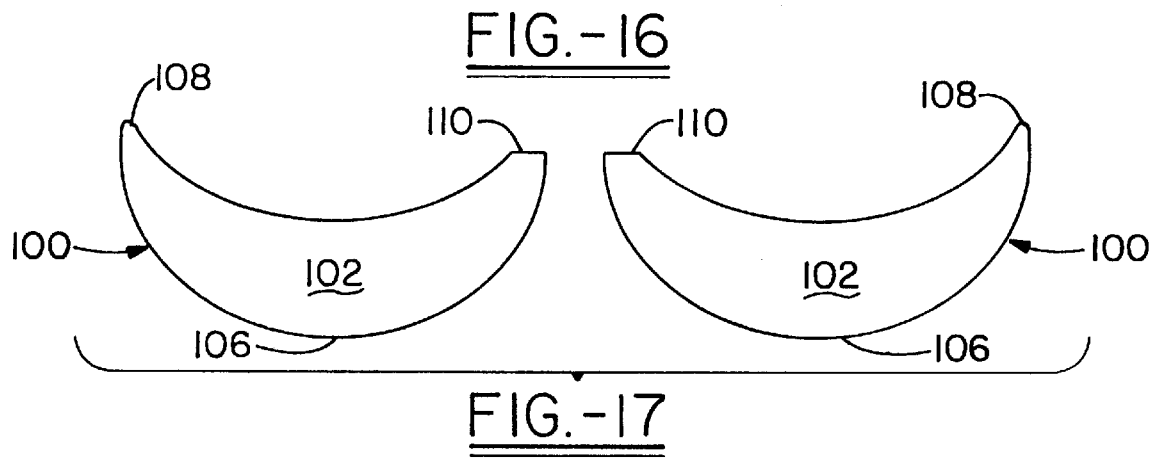
FIG. 17 is an elevational view of an alternative absorbent breast pad.
Figure 18:
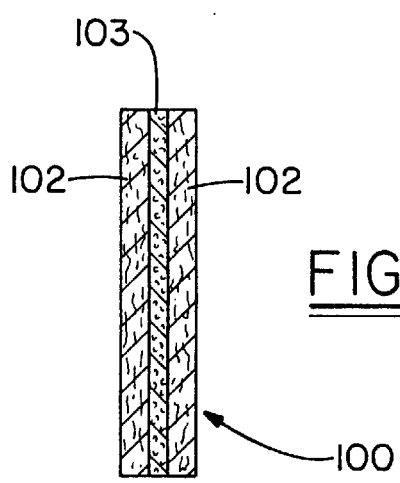
FIG. 18 is an enlarged side view in cross-section of the alternative breast pads.

Referring now to FIGS. 12–14, it can be seen that a breast pad with many of the same attributes as the other embodiments is designated generally by the numeral 80. The breast pad 80 includes opposed layers of substantially absorbent material 82 and a layer of moisture retention material 83 disposed therebetween. The breast pad 80 provides longitudinal edges 84 that are connected by opposed ends 86. The edges 84 and the ends 86 are sealed to attach the layers 82 and 83 to one another. One longitudinal edge 84 provides a plurality of v-shape notches 88, each of which has a pair of notch edges 90 that terminate at a vertex 92. Provided on the opposed longitudinal edge 84 are a plurality of slits 94 which are aligned with the vertex 92 of the opposed notch 88. As best seen in FIGS. 13 and 14, the breast pad 80 is placed between the breast 34 and the midriff 36 and curved upwardly so that the notch edges 90 are directed toward one another and so that the edges of the slits 94 are pulled away from one another. It will be appreciated then that one breast pad 80 is used for each breast. Referring now to FIGS. 15–18, it can be seen that an alternative embodiment of the breast pad is designated generally by the numeral 100. The substantially crescent-shaped breast pad 100 includes opposed layers of absorbent material 102 and a layer of moisture retention material 103 disposed therebetween. The breast pad 100 includes a concave edge 104 opposite a convex edge 106. The concave edge 104 and convex edge 106 are connected at their respective ends by an outer connection point 108 and an inner connection point 110. An attachment flag 112 extends upwardly from the inner connection point 110 so that adjacent breast pads 100 may be connected to one another. In particular, the attachment flag 112 includes a backing layer 114 opposite an adhesive layer 116. A release layer 117 may be provided over the adhesive layer 116 and removed when the adjacent breast pads 100 are to be attached to one another. Accordingly, the adhesive layer 116 may be attached to an adjacent breast pad 100 by applying the adhesive layer 116 to a like adhesive layer 116 or the backing layer 114. Accordingly, adjacent breast pads 100 may be joined and placed between the breast 34 and midriff 36 as shown in FIG. 16. The attachment flag 112 may be provided in various sizes to allow for positional adjustment of the breast pads 100 where desired. Alternatively, and as seen in FIG. 17, adjacent breast pads 100 may be provided without an attachment flag 112 to allow for easier positional adjustment. This feature eliminates the need to position the attachment flags 112 near each other.

The advantages of the breast pads 80 and 100 are generally the same as the advantages described above for the breast pads 40, 60 and 80. The breast pads 80 and 100 are positioned so that both absorbent layers 82, 102 pull moisture away from the skin and into their respective layers of moisture retention material 83 and 103, respectively. Additionally, the breast pads 80 and 100 may be employed in those situations where a brassiere is not used.

Thus it can be seen that the objects of the invention have been satisfied by the structure and use of the invention as presented above. While in accordance with Patent Statutes, only the best mode preferred embodiment of the invention have been presented and described in detail, it is to be understood that the invention is not limited thereto or thereby. Accordingly, for an appreciation of the true scope and breadth of the invention, reference should be made to the following claims.

What is claimed is:

1. A breast pad, supportable by a brassiere, for absorbing moisture around a breast area including an underside of a breast and a midriff, comprising:

a layer of absorbent material adjacent a layer of moisture retention material, said layers including two opposed longitudinal edges joined by two opposed ends and a plurality of notches in at least one of said longitudinal edges which allow said layers to be shaped to conform to a cup surface of a brassiere, and a releasable adhesive material at least partially disposed on said layer of moisture retention material and facing away from said layer of absorbent material, wherein the releasable adhesive material is affixable to the cup surface of the brassiere so that said layer of absorbent material is contactable with skin around the underside of the breast and the midriff.

2. The breast pad according to claim 1, wherein the other of the two opposed longitudinal edges also has a plurality of notches, and wherein a fold line is provided at about a mid-point between and substantially parallel with said longitudinal edges, a first portion of said releasable adhesive material being adherable to an inner cup surface of the brassiere and a second portion of said releasable material being adherable to an outer cup surface of the brassiere, said notches providing opposed notch edges that are positioned closer to one another when said layers are shaped to conform to the cup surface.

3. The breast pad according to claim 1, wherein only said one of said longitudinal edges has a plurality of notches and the other of said longitudinal edges has a plurality of slits which allow said layers to be shaped to conform to the cup surface, said breast pad further including a plurality of attachment tabs extending from said other of said longitudinal edges and wherein said releasable adhesive is disposed on one side of said attachment tabs which is attachable to an outer cup surface of the brassiere.

4. The breast pad according to claim 3, wherein said notches provide opposed notch edges that are positioned closer to one another when said layers are shaped to conform to the cup surface.

5. A solitary breast pad for absorbing moisture between a breast and a midriff, comprising:

opposed layers of absorbent material having a layer of moisture retention material disposed therebetween, all said layers having two opposed longitudinal edges joined at opposed ends, a plurality of notches along one of said longitudinal edges and a plurality of slits along the other of said longitudinal edges, wherein said notches have notch edges that are directable toward one another to conform the shape of said layers to an underside of the breast, between the breast and the midriff, and all said layers provided in a substantially flat configuration and being positionable between the breast and the midriff such that one is precluded from contacting the other and enabling absorption of moisture from both the breast and the midriff.

6. The solitary breast pad according to claim 5, wherein said slits are aligned substantially opposite respective vertices of said plurality of notches to allow said notch edges to abut one another when said layers of material are conformed.

* * * * *